(12) United States Patent
Ocaranza Jeraldino et al.

(10) Patent No.: US 9,132,164 B2
(45) Date of Patent: Sep. 15, 2015

(54) PHARMACEUTICAL COMPOSITIONS COMPRISING ANGIOTENSIN-(1-9), DERIVATIVES THEREOF, OR A VECTOR EXPRESSING ACE2, USEFUL FOR TREATING CARDIOVASCULAR, PULMONARY, CEREBRAL, AND/OR RENAL REMODELING

(75) Inventors: María Paz Ocaranza Jeraldino, Santiago (CL); Sergio Lavandero González, Santiago (CL); Jorge Jalil Milad, Santiago (CL); Mario Chiong Lay, Santiago (CL)

(73) Assignees: PONTIFICIA UNIVERSIDAD CATOLICA DE CHILE, Santiago (CL); UNIVERSIDAD DE CHILE, Santiago (CL)

( * ) Notice: Subject to any disclaimer, the term of this patent is extended or adjusted under 35 U.S.C. 154(b) by 579 days.

(21) Appl. No.: 12/998,910

(22) PCT Filed: Dec. 15, 2009

(86) PCT No.: PCT/CL2009/000029
§ 371 (c)(1),
(2), (4) Date: Nov. 7, 2011

(87) PCT Pub. No.: WO2010/069090
PCT Pub. Date: Jun. 24, 2010

(65) Prior Publication Data
US 2012/0172301 A1    Jul. 5, 2012

(30) Foreign Application Priority Data
Dec. 15, 2008   (CL) .................................. 3736-2008

(51) Int. Cl.
*A61K 38/08*   (2006.01)

(52) U.S. Cl.
CPC .................................. *A61K 38/085* (2013.01)

(58) Field of Classification Search
None
See application file for complete search history.

(56) References Cited

U.S. PATENT DOCUMENTS 6,592,865 B2    7/2003   Parry et al.

FOREIGN PATENT DOCUMENTS

EP       1348440 A1 *  10/2003

OTHER PUBLICATIONS

Iwata et al., "Angiotensin-(1-7) binds to specific receptors on cardiac fibroblasts to initiate antifibrotic and antitrophic effects", Am J Physiol Heart Circ Physiol, 2005, pp. H2356-H2363.*
Grobe et al., "Prevention of angiotensin II-induced cardiac remodeling by angiotensin-(1-7)", Am J Physiol Heart Circ Physiol, 2007; first published 2006, pp. H736-H742.*
Lefebvre et al., "Modification of the pulmonary renin-angiotensin system and lung structural remodeling in congestive heart failure", Clinical Science, 2006, pp. 217-224.*
Edgely et al., "Evidence for renal vascular remodeling in angiotensin II-induced hypertension", Journal of Hypertension, 2003, pp. 1401-1406.*
Grobe, "The role of angiotensin-(1-7) in cardiovascular physiology", 2006, Order No. 3224545, University of Florida. ProQuest Dissertations and Theses, pp. 1-134. Retrieved from http://search.proquest.com/docview/305327183?accountid=14753.*
Jackman et al., "Angiotensin 1-9 and 1-7 Release in Human Hear Role of Cathepsin A", Hypertension, 2002, pp. 976-981.*
Tanaka et al. ,"Effects of Bradykinin on Cardiovascular Remodeling in Renovascular Hypertensive Rats", Hypertension Research, 2004, pp. 865-875.*
Flores-Munoz et al.,"Angiotensin-(1-9) Attenuates Cardiac Fibrosis in the Stroke-Prone Spontaneously Hypertensive Rat via the Angiotensin Type 2 Receptor", Hypertension, 2012 pp. 300-307.*
T. Hattori, et al; "Long-Term Inhibition of Rho-Kinase Suppresses Left Ventricular Remodeling After Myocardial Infarction in Mice", Circulation, Lippincott Williams & Wilkins, US LNKD-DOI:10.1161/01.CIR.0000127939.16111.58, vol. 109, No. 18, May 11, 2004, pp. 2234-2239, XP009037379, ISSN: 0009-7322.
Matthew J Huentelman, et al; "Protection from angiotensin II-induced cardiac hypertrophy and fibrosis by systemic lentiviral delivery of ACE2 in rats", Experimental Physiology, Cambridge University Press, Cambridge, GB LNKD-DOI:10.1113/EXPPHSIOL. 2005.031096, vol. 90, No. 5, Sep. 1, 2005, pp. 783-790, XP002486170, ISSN: 0958-0670 [retrieved on Jul. 27, 2005].
M.J. Katovich, et al; "Angiotensin-(1-7) as an antihypertensive, antifibrotic target", Current Hypertension Reports 200806 GB LNKD-DOI:10.1007/S11906-008-0043-9, vol. 10, No. 3, Jun. 2008, pp. 227-232, XP002584629 ISSN:1522-6417.
International Search Report: mailed Jun. 17, 2010; PCT/CL2009/000029.

* cited by examiner

Primary Examiner — Karlheinz R Skowronek
Assistant Examiner — Lianko Garyu
(74) Attorney, Agent, or Firm — Ladas & Parry LLP

(57) ABSTRACT

A pharmaceutical composition is provided having an effective amount of angiotensin-(1-9) and at least one pharmaceutical acceptable carrier, excipient, stabilizer, diluent, and/or adjuvant. Also provided is a method of using the pharmaceutical composition for inhibiting and/or reducing cardiovascular remodeling.

9 Claims, 6 Drawing Sheets

Figure 1:
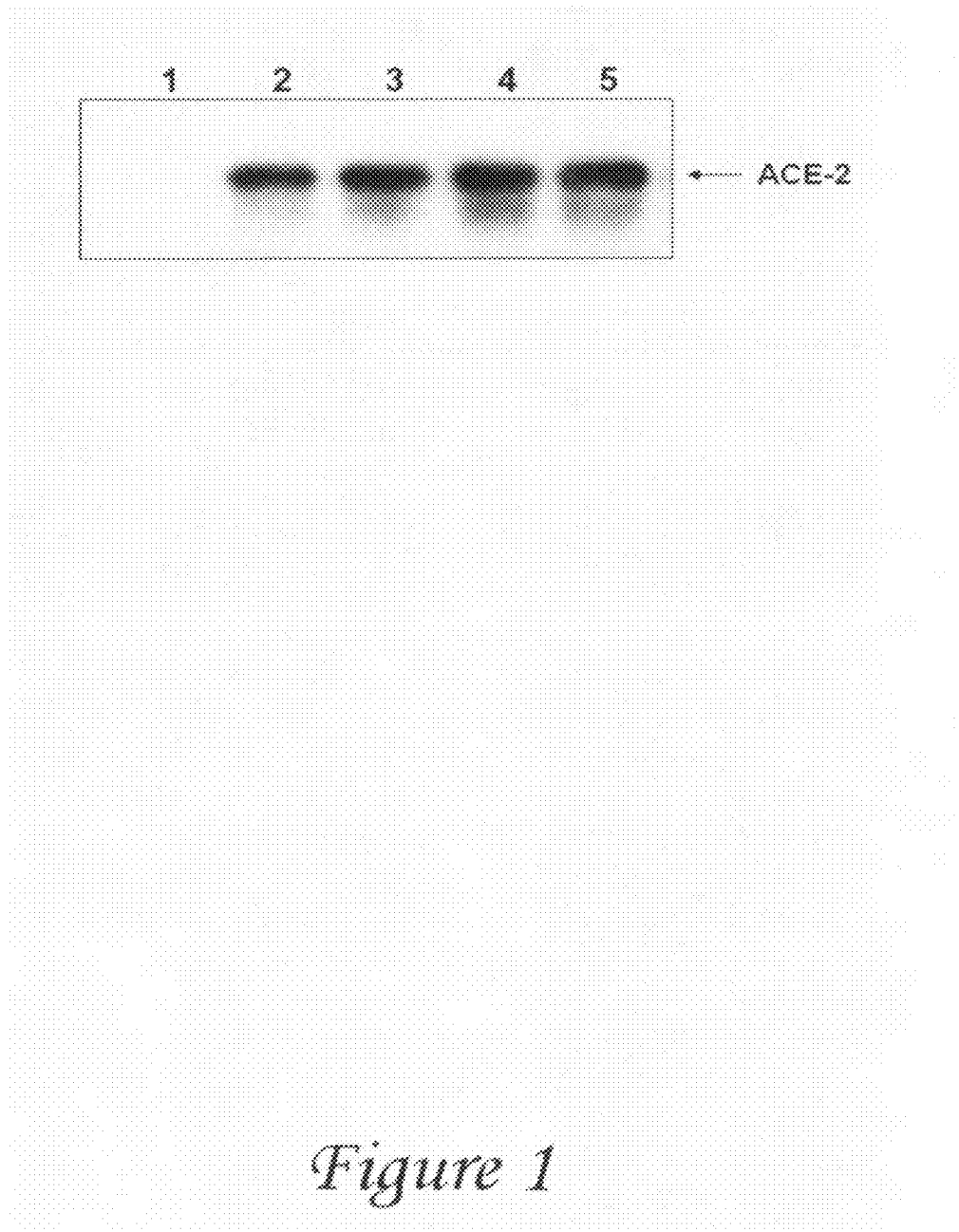

SEQUENCE LISTING

```
<160> NUMBER OF SEQ ID NOS: 7

<210> SEQ ID NO 1
<211> LENGTH: 14
<212> TYPE: PRT
<213> ORGANISM: Homo sapiens

<400> SEQUENCE: 1

Asp Arg Val Tyr Ile His Pro Phe His Leu Leu Val Tyr Ser
1               5                   10

<210> SEQ ID NO 2
<211> LENGTH: 10
<212> TYPE: PRT
<213> ORGANISM: Homo sapiens
```

```
<400> SEQUENCE: 2

Asp Arg Val Tyr Ile His Pro Phe His Leu
1               5                   10

<210> SEQ ID NO 3
<211> LENGTH: 8
<212> TYPE: PRT
<213> ORGANISM: Homo sapiens

<400> SEQUENCE: 3

Asp Arg Val Tyr Ile His Pro Phe
1               5

<210> SEQ ID NO 4
<211> LENGTH: 7
<212> TYPE: PRT
<213> ORGANISM: Homo sapiens

<400> SEQUENCE: 4

Arg Val Tyr Ile His Pro Phe
1               5

<210> SEQ ID NO 5
<211> LENGTH: 6
<212> TYPE: PRT
<213> ORGANISM: Homo sapiens

<400> SEQUENCE: 5

Val Tyr Ile His Pro Phe
1               5

<210> SEQ ID NO 6
<211> LENGTH: 9
<212> TYPE: PRT
<213> ORGANISM: Homo sapiens

<400> SEQUENCE: 6

Asp Arg Val Tyr Ile His Pro Phe His
1               5

<210> SEQ ID NO 7
<211> LENGTH: 7
<212> TYPE: PRT
<213> ORGANISM: Homo sapiens

<400> SEQUENCE: 7

Asp Arg Val Tyr Ile His Pro
1               5
```

PHARMACEUTICAL COMPOSITIONS COMPRISING ANGIOTENSIN-(1-9), DERIVATIVES THEREOF, OR A VECTOR EXPRESSING ACE2, USEFUL FOR TREATING CARDIOVASCULAR, PULMONARY, CEREBRAL, AND/OR RENAL REMODELING

FIELD OF THE INVENTION

The present invention relates to the field of the angiotensin (1-9) peptide or derivatives thereof which are chemical or biological equivalents. Particularly, the present invention relates to pharmaceutical compositions comprising angiotensin (1-9) and/or derivatives thereof and the anti-remodeling effects of such peptides, especially in cardiovascular, cerebral, pulmonary and/or renal remodeling, and more particularly to the anti-hyperthrophic, anti-hyperplastic, antifibrotic, cytoprotective, antiapoptotic, antinecrotic, anti-autophagic, antioxidant, anti-inflammatory, and inhibitory effects of collagen synthesis on the heart, lung, kidney and blood vessels. Additionally, this invention relates to the field of elevating blood and/or tissue concentrations of angiotensin (1-9) peptide through increased endogenous production of angiotensin (1-9) through a vector expressing ACE2, the enzyme responsible for the endogenous production of angiotensin (1-9).

STATE OF THE ART

Increased activation of the renin-angiotensin system (RAS), specifically, the classic route with more activity of the angiotensin I-converting enzyme (ACE) and higher levels of antiotensin II, have been identified as major determiners of the etiology of hypertension (HT), heart failure, in physiopathological processes of cardiovascular remodeling, diastolic dysfunction and disorders of vasodilation in resistance arteries. Therefore, ECA and angiotensin II constitute one the main therapeutic target of the current HT treatment (Varagic & Frohlich, J. Mol. Cell. Cardiol. 34:1435-42, 2002).

SRA cascade is initiated by the action of renin on circulating hepatic angiotensinogen. This reaction produces angiotensin I which is physiologically inactive. Angiotensin I is transformed into the biologically active angiotensin II octapeptide through the action of ACE (Okunishi et al, Jpn J. Pharmacol. 62:207-10, 1993). ACE is a zinc-dependent metallopeptidase, mainly found in lungs, but also in the heart, blood vessels, kidney as well as plasma (Campbell, J. Cardiovasc. Pharmacol. 10:S1-S8, 1987; Johnston et al, J. Hypertens. Suppl. 10:S13-26, 1992). In human beings, tissue angiotensin II is also produced by other enzymes such as kinase and tissue plasminogen activating factor (Reilly et al, J. Biol. Chem. 257:8619-22, 1982; Gibbons & Dzau, N. Engl. J. Med. 19:1431-8, 1994). ACE is also responsible for catabolism and inactivation of vasodilators such as bradykinins (BKs). ARS is involved in the development of HT (Dzau, J Hypertens Suppl. 6:7-12, 1988; Bader et al, Exp. Physiol. 85:713-731, 2000; Bader et al, J Mol. Med. 79:76-102, 2001), with regard to insulin resistance (Yavuz et al, J. Renin. Angiotensin Aldosterone Syst. 4:197-203, 2003; Henriksen & Jacob, Diabetes Obes. Metab. 5: 214-22, 2003), metabolism of nitric oxide (Liu and Person, Hypertension 43:649-53, 2004), oxidative stress (Zhou et al, Am. J. Hypertension 17:167-71, 2004), and cardiac and vascular smooth muscle hypertrophy (Higashi et al, Circ. Res. 93:767-75, 2003; Yamakawa et al, Eur J. Pharmacol. 478:39-46, 2003).

Angiotensin II exerts its action on target cells via G protein-coupled receptors, subtypes 1 and 2 (ATR 1 and ATR 2, respectively). Activation of ATR1 causes most of the cardiovascular actions of angiotensin II such as vasoconstriction, mitogenic and hypertrophic effects, inflammatory response and water and salt retention (de Gasparo et al, J. Renin Angiotensin Aldosterone Syst. 1:151-8, 2000). These effects are mediated by a complex interaction of intracellular signaling pathways involving several phospholipases (PLC, PLD, PLA2), stimulation of NAD(P)H oxidase and reactive oxygen species ($O_2^-$, $H_2O_2$), gene transcription activation (protooncogenes: c-foc, c-jun, c-myc), and tyrosine kinase activation (Src, JAK/STAT, FAK, Pyk2, p130Cas and Pi3-kinase). Some of these actions may be, directly or indirectly, mediated by transactivation of tyrosine kinase receptors (Touyz & Berry, Braz. J. Med. Biol. Res. 35:1001-15, 2002). Unlike ATR1-madiated actions, ATR2 exerts effects such as apoptosis, natriuresis and vasodilation mediated by BKs and nitric oxide (NO) (de Gasparo et al, J. Renin Angiotensin Aldosterone Syst. 1:151-8, 2000).

Recently, a pathway parallel to ARS initiated by a homologous angiotensin I-converting enzyme (ACE-2) has been discovered. (Tipnis et al, J. Biol. Chem. 275: 33238-43, 2000; Donoghue et al, Circ. Res. 87:e1-9, 2000). Originally, this enzyme was found in testicles, kidneys and heart, however, real-time PCR studies conducted later showed that its expression is also found in the gastrointestinal tract, brain, lungs, aorta, and liver (Harmer et al, FEBS Lett. 532:107-10, 2002; Ferrario, Hypertension 47:515-21, 2006). At cellular level, ACE2 has been mainly found in renal tubulus epithelium, macrophages, cardiomyocytes, large and small artery endothelium, and smooth muscle of these vessels (Burell et al, Eur. Heart J. 26:369-75, 2005). ACE2 exhibits 40% homology in its catalytic domain with ACE and it is an ectoenzyme whose catalytic sites are oriented toward the extracellular space and therefore, it is capable of hydrolyzing extracellular peptides. Additionally, like ACE, the ACE2 is capable of detaching from cell surface and it exhibits a topology of a type I integral membrane protein. Despite this similitude, ACE-2 differs from ACE in substrate specificity and the lack of inhibition by ACE classic inhibitors.

In ARS, ACE2 competes with ACE for hydrolysis of inactive angiotensin I decapeptide to form angiotensin-(1-9) (Donoghue et al, J. Mol. Cell. Cardiol. 35:1043-53, 2003), therefore, the amount of angiotensin I available to generate angiotensin II through the action of ACE is reduced. Even though the effects of angiotensin-(1-9) in the heart and kidneys have not been described (Danilczyk & Penninger, Circ. Res. 98:463-71, 2006), several studies have shown that angiotensin-(1-9) potentiates angiotensin II-mediated vasoconstriction in aortic rings from rats and that possesses vasopressor effects on conscious rats (Huang et al, J. Biol. Chem. 278:15532-40, 2003). Additionally, it has been found that angiotensin-(1-9) levels in human an rat plasma are higher than those of angiotensin II (Johnson, Peptides 10:489-92, 1989), and that this peptide is accumulated in iACE-treated animals (Drummer, Biochem. Pharmacol. 39:513-8, 1990). Other studies indicate that angiotensin-(1-9) favors bradykinin binding to its B2 receptor, probably due to conformational changes in the ACE-B2 receptor complex (Erdos et al, J. Mol. Cell. Cardiol. 34:1569-76, 2002).

ACE2 catalytic efficiency is (400-fold) higher to hydrolyze angiotensin II than angiotensin I and to form the angiotensin-(1-7) vasodilator peptide (Donoghue et al, Circ. Res. 87: e1-9, 2000, Vickers et al, J. Biol. Chem. 277: 14838-43, 2003; Rice et al, Biochem. J. 383:45-51, 2004). The latter is also generated by hydrolyzing angiotensin I through the action of neutral endopeptidase (NEP), prolil endopeptidases or ACE (Welches et al, Life Sci. 52:1461-80, 1993; Vickers et al, J. Biol. Chem. 277: 14838-43, 2003). Therefore, ACE2 plays a key role in the balance of the vasoconstrictor and proliferative activity of angiotensin II via its ATR1 by increasing the angiotensin-(1-7) levels (Der Sarkissian et al, Prog. Biophys. Mol. Biol. 91:163-98, 2005).

However, there is no evidence that indicates whether angiotensin-(1-9) and/or derivatives thereof possess effects that prevent, revert, inhibit, and/or reduce the cardiovascular, pulmonary, cerebral, or renal remodeling.

Angiotensins relate to angiotensinogen-derived peptides which are obtained by proteolysis. These peptides are:
Angiotensinogen*: Asp-Arg-Val-Tyr-Ile-His-Pro-Phe-His-Leu-Leu-Val-Tyr-Ser (SEQ ID NO:1) Angiotensin 1: Asp-Arg-Val-Tyr-Ile-His-Pro-Phe-His-Leu (SEQ ID NO:2) Angiotensin II: Asp-Arg-Val-Tyr-Ile-His-Pro-Phe (SEQ ID NO:3) Angiotensin III: Arg-Val-Tyr-Ile-His-Pro-Phe (SEQ ID NO:4) Angiotensin-IV: Val-Tyr-Ile-His-Pro-Phe (SEQ ID NO:5) Angiotensin-(1-9): Asp-Arg-Val-Tyr-Ile-His-Pro-Phe-His (SEQ ID NO:6) Angiotensin-(1-7): Asp-Arg-Val-Tyr-Ile-His-Pro (SEQ ID NO:7) *The first amino acid of the sequences corresponds to the R amino-terminal end: the rest of the sequence, to the angiotensinogen. Several physiological and biological functions have been described for different angiotensins.

```
Angiotensinogen*:
Asp-Arg-Val-Tyr-Ile-His-Pro-Phe-His-Leu-Leu-Val-

Tyr-Ser

Angiotensin 1:
Asp-Arg-Val-Tyr-Ile-His-Pro-Phe-His-Leu

Angiotensin II:
Asp-Arg-Val-Tyr-Ile-His-Pro-Phe

Angiotensin III:
Arg-Val-Tyr-Ile-His-Pro-Phe

Angiotensin-IV:
Val-Tyr-Ile-His-Pro-Phe

Angiotensin-(1-9):
Asp-Arg-Val-Tyr-Ile-His-Pro-Phe-His

Angiotensin-(1-7):
Asp-Arg-Val-Tyr-Ile-His-Pro
*The first amino acid of the sequences corresponds
to the R amino-terminal end: the rest of the
sequence, to the angiotensinogen.
Several physiological and biological functions
have been described for different angiotensins.
```

Des-aspartate-angiotensin I has been described to be used for the treatment and/or prevention of cardiac hypertrophy (U.S. Pat. No. 5,773,415) and neointimal formation or restenosis (U.S. Pat. No. 6,100,237). Angiotensin II is involved in cardiac hypertrophy and neointimal formation. Exogenous administration of angiotensin II potentiates cardiac hypertrophy (Dostal & Baker, Am. J. Hypertens., 5:276-280, 1991) and neointimal formation (Osterrieder et al, Hypertension. 18:II60-4, 1991; Daemen et al, Circ. Res. 68:450-6, 1991).

Angiotensin III mediates the induction of receptor AT2-dependent natriuresis. Induce vasoconstriction and release of aldosteron (Fyhrquist & Saijonmaa, J. Intern. Med. 264:224-36, 2008).

Angiotensin IV, a metabolite secondary to angiotensin II, possesses anti-hypertrophic activity and also inhibits neointimal formation (EP1846017).

Angiotensin-(1-7) is involved in the actions which oppose the actions of angiotensin II. It has been described as a vasodilator-inducing peptide, with hyperintensive and anti-fibrotic effects. (Katovich et al, Curr. Hypertens. Rep. 10:227-32, 2008).

However, neither physiological and/or biological functions for angiotensin-(1-9) peptide, nor medical uses and/or medical treatment comprising administration and/or use of angiotensin-(1-9) and/or derivatives thereof in medicine have been described in the previous art. The present invention relates and solves the problem of the lack of information with regard to biological and/or physiological actions of angiotensin-(1-9), describes the anti-remodeling effects of this peptide, and provides procedures to elevate the plasma and/or tissue angiotensin-(1-9) concentrations, as well as novel uses and/or pharmaceutical compositions of angiotensin-(1-9) or derivatives thereof.

DETAILED DESCRIPTION OF THE INVENTION

There are several procedures to elevate plasma and/or tissue angiotensin-(1-9) concentration. The elevation of plasma and/or tissue angiotensin-(1-9) concentration levels is associated with cardiovascular, renal, pulmonary and cerebral remodeling reduction phenomena (see example 10). In the present invention, we describe that the elevation of plasma angiotensin-(1-9) concentration may be achieved by:

a) Administering pharmaceutical compositions containing the angiotensin-(1-9) peptide (see example 11).
b) Administering drugs that elevate the homologous angiotensin I-converting enzyme (ACE2), thereby increasing the endogenous production of angiotensin-(1-9), causing plasma and/or tissue elevation of such peptide (see example 10).
c) Administering a gene that overexpresses the homologous angiotensin I-converting enzyme (ACE2), enzyme responsible for endogenous production of angiotensin-(1-9) (see examples 7 and 8).

The present invention relates to a pharmaceutical composition comprising an effective amount of angiotensin-(1-9) or derivatives thereof, and at least one pharmaceutically acceptable carrier, excipient, stabilizer, diluent and/or adjuvant. The present invention also describes the use of such pharmaceutical composition for manufacturing medicaments useful for preventing, reverting, inhibiting, and reducing cardiovascular, pulmonary, cerebral, or renal remodeling. Additionally, the present invention describes the use of the angiotensin-(1-9) peptide or derivatives thereof to manufacture medicaments and/or pharmaceutical compositions useful for preventing, reverting, inhibiting, and/or reducing cardiovascular, pulmonary, cerebral, or renal remodeling, specially in animals or humans, and more specifically, in patients in need thereof. The present invention also provides, through the use of angiotensin-(1-9) and/or derivatives thereof, a method to prevent, revert, inhibit, and/or reduce cardiovascular, pulmonary, renal and/or cerebral remodeling.

Moreover, this invention comprises a method to prevent, revert, inhibit and/or reduce cardiovascular, pulmonary, cerebral, or renal remodeling which consists of elevating plasma and/or tissue concentration of angiotensin (1-9) peptide or derivatives thereof through a pharmaceutical composition containing an ACE2 expressing vector, enzyme responsible for endogenously producing angiotensin-(1-9). These vectors correspond to adenovirus, retrovirus, lentivirus or adeno-associated virus containing the ACE2 encoding gene. According to the invention, the method to prevent, revert, inhibit and/or reduce cardiovascular, pulmonary, cerebral, or renal remodeling, comprises administering to the patient an effective amount of angiotensin-(1-9) and/or at least one derivative of angiotensin-(1-9). The present invention also provides a pharmaceutical composition comprising an effective amount of angiotensin-(1-9) and/or at least one derivative of angiotensin-(1-9), and at least one pharmaceutically acceptable excipient, carrier, diluent, stabilizer, and/or adjuvant. The composition is preferably intended for the use of preventing, reverting, inhibiting, and/or reducing cardiovascular, pulmonary, renal, and/or cerebral remodeling in a patient or animal in need thereof, and comprises administering such pharmaceutical composition to the patient. The patient may be a human being or an animal. The use of such medicament or pharmaceutical composition is envisaged to elevate plasma and/or tissue angiotensin-(1-9) levels, and/or at least one of derivatives thereof. Particularly, it aims at elevating levels of such peptides in the organism, preferably, in plasma, heart, kidney, lungs, brain and/or vascular bed.

The medicament or pharmaceutical composition of the present invention comprising an effective amount of angiotensin-(1-9), and/or at least one derivative of angiotensin-(1-9) may be applied via any known route of medication administration already. Particularly, such medicament or pharmaceutical composition will be applied via injection and/or parenteral route (for example, but not limited to, intravenous, intra-arterial, intramuscular, intraperitoneal, transdermal, subcutaneous, and via direct injection into several organs, including heart, lungs, kidney and brain), by inhalation, by the use of continuous release pharmaceutical composition, by the use of releasing pumps, by suppositories, or via oral route. Such administration can be as a single dose, multiple dose or continuous administration. Angiotensin-(1-9) and/or derivatives thereof, pharmaceutical compositions containing it(them) and/or medicaments containing it(them) according to the present invention can be solid or liquid, including, lozenges, wafers, pills, tablets, capsules, suspensions, or solutions containing at least one pharmaceutically acceptable excipient, carrier, diluent, stabilizer, and/or adjuvant. Pharmaceutically acceptable excipients, carriers, diluents, stabilizers, and/or adjuvants are well known by those skilled in the art, and they can be solid, liquid, or a combination thereof. Thus, pharmaceutical compositions or medicaments can take the form of tablets, pills, capsules, wafers, powder, coated formulations, sustained-release formulations, erodible formulations, implanted devices, or components derived from such devices, microsphere formulations, solutions, suspensions, elixirs, aerosols and the like. Liquid carriers, diluents, and/or excipients are preferably water, saline, dextrose solution, and glycol solution, especially when parenteral route and/or injection are used as a route of administration. The carrier and/or diluent can be also an oil, for example, those derived from petroleum, oils of animal, vegetable, or synthetic origin. Specific examples of preferred oils of the invention include peanut oil, soybean oil, mineral oil, sesame oil, corn oil, sunflower oil, and the like. Some of the preferred excipients of the invention include starch, cellulose, talc, glucose, lactose, sucrose, gelatin, malt, rice, flour, chalk, silica gel, magnesium stearate, glycerol monostearate, sodium chloride, dried skim milk, glycerol, propylene glycol, water, ethanol, and the like. Other carriers, diluents, stabilizers, excipients and/or adjuvants not mentioned herein, are apparent to those skilled in the art. The composition or medicament of the present invention may be subjected to conventional pharmaceutical processes such as sterilization, and may contain other conventional pharmaceutical additives such as preservatives, stabilizers, emulsifying agents, wetting agents, salts to adjust osmotic pressure, buffers, or pH buffering agents, and the like. Carriers, stabilizers, diluents, excipients, and/or adjuvants can be found in Martin, "Remington's Pharmaceutical Sciences", 15" Ed.; Mack Publishing Co., Easton (1975); see for example pages 1405-1412 and 1461-1487. Such compositions generally contain an effective amount of the active compound with a suitable amount of one or several carriers, stabilizers, diluents, excipients and/or adjuvants, so that the dose and the proper way of administering angiotensin-(1-9) and/or derivatives thereof to the patient can be prepared. In the practice, in the treatment methods of the invention, the particular dosage of a pharmaceutical composition or medicament to be administered to the patients will depend on several variables including the disease status, seriousness of the disease, administration schedule, age, patient's physical characteristics, etc. Proper dosage can be established using clinical approximations known by those skilled in the art. Additionally, angiotensin-(1-9) and/or at least one of its derivatives, the medicament or the pharmaceutical composition of the present invention may be administered with at least one pharmaceutical compound. The phrase "at least one pharmaceutical compound" relates to an angiotensin I-converting enzyme inhibitor, an angiotensin II (AT1) receptor antagonist, an L-calcium channel antagonist, a Rho kinase inhibitor, and/or a diuretic. The administration of any of these pharmaceutical compounds is capable per se of elevating plasma angiotensin-(1-9) concentration. Example 10 describes that the administration of a converting enzyme inhibitor (enalapril) or the administration of a angiotensin II receptor antagonist (candesartan) increase plasma and/or tissue angiotensin-(1-9) levels and that such increment is associated to a reduction of the cardiovascular, renal, pulmonary and cerebral remodeling.

Examples of the angiotensin I-converting enzyme (ACE) are lisinopril, enalapril, captopril, zofenopril, ramipril, quinapril, perindopril, benazepril and fosinopril. Examples of angiotensin II receptor antagonists (AT1) are valsartan, telmisartan, losartan, irbesartan, olmesartan, candesartan, eprosartan, and saralasin. Examples of L-calcium channel antagonists are the dihydropyridines (nicardipine, nifedipine, amlodipine, felodipine, nitrendipine, nisoldipine, isradipine, nimodipine), the benzotiazepines (diltiazem, clentiazem) and the phenylalkylamines (verapamil, gallopamil, anipamil, RO5967, falipamil). Examples of Rho kinase inhibitors are fasudil, hydroxyl-fasudil, 3-(4-piridil)-1H-indol, (S)-(+)-2-methyl-1-[(4-methyl-5-isoquinolinyl)sulfonyl]homopiperazine, N-(4-piridyl)-N'-(2,4,6-trichlorophenyl)urea. Examples of diuretics are thiazidic duiretics (bendroflumethiazide, benzithiazide, chlorothiazide, chlortalidone, hydrochlorothiazide, hydroflumethiazide, indapamide, metyclothiazide, metolazone, polythiazide, kinetazone, trichlormethiazide, xipamide), loop diuretics (furosemide, torasemide, bumetanide, etacrinic acid), carbonic anhydrase inhibitor diuretics (acetazolamide, dorzolamide), potassium-saving diuretics (amiloride, triamterene), potassium saving diuretics which are aldosterone antagonists (spironolactone, canrenoate, eplerenone) and osmotic diuretics (mannitol).

The present invention also considers as part of the invention increasing the plasma and/or tissue angiotensin-(1-9) levels by increasing its production and/or inhibiting its degradation. Additionally, the present invention involves exacerbation, activation, and/or induction of intracellular transduction signals activated by angiotensin-(1-9) and/or derivatives thereof. The increased production of angiotensin-(1-9) and/or derivatives thereof can be achieved by increasing or overexpressing the homologous angiotensin I-converting enzyme (ACE2). The increased activity of ACE2 can be achieved by inhibiting the angiotensin I converting enzyme (ACE), specifically, with the use of inhibitors of this enzyme, particularly drugs which are already known in the art such as lisinopril, enalapril, captopril, zofenopril, ramipril, quinapril, perindopril, benazepril and fosinopril. ACE2 overexpression can be achieved by introducing one or several copies of ACE2 encoding gene into the organism. The introduction of the gene encoding ACE2 into the organism is achieved by techniques already described in the art including naked DNA, liposomes (particularly cationic liposomes) and by the use of viral vectors. In the present invention, it is more particularly described, without limitation as to any other viral vectors, the use of adenoviral, retroviral, lentiviral vectors and adeno-associated virus containing the ACE2 encoding gene within its genetic material. It is also known by those skilled in the art that for such gene to be active it requires that its expression be commanded by a promoter and that the gene ends at a terminator. The aforementioned vectors of this patent include flanking the gene encoding ACE2, a promoter and a terminator. It is also part of the present invention that vectors containing the gene encoding ACE2 have DNA sequences which are important to enhance mRNA stability, as well as sequences which allow normal transduction of mRNA into protein. Likewise, several promoter structures that allow constitutive or regulated expression of the desired genes are well known in the art. The present invention also considers that the promoter regulating the expression of the ACE2-encoding gene be constitutive or regulated in nature by means of gene induction or repression. In the present invention angiotensin-(1-9) is used as an example of angiotensin-(1-9) and/or derivatives thereof. Additionally, rats are used as an example of a mammal to whom the treatment method can be applied, and angiotensin-(1-9) and/or derivatives thereof in the form of medicaments and/or pharmaceutical composition can be assayed. Animal models for studying cardiovascular, pulmonary, cerebral and/or renal remodeling, including small mammals such as rats, have been widely accepted in previous art (Everette et al, Hypertension, 23:587-593, 1994; Indolfi et al, Circulation, 92:1230-1235, 1995). Using rat model does not exclude its use in humans or other type of animal in need of such treatment.

In the present invention, remodeling refers to the complex changes undergone by organs subjected to stress conditions. Organs particularly preferred in this invention to prevent remodeling by using angiotensin-(1-9) or derivatives thereof comprise the heart, blood vessels, kidney, brain, and lungs, without excluding other organs that could undergo remodeling and could be treated with angiotensin-(1-9) or derivatives thereof. Remodeling must be understood in its broadest possible form and it comprises a number of cellular, biochemical and/or physiological processes, which comprise one or every process selected among cardiomyocyte hypertrophy, neointimal formation, fibroblast hyperplasia, smooth muscle cell hyperplasia, cytoprotection, fibrosis, collagen deposit, inflammation, apoptosis, necrosis and/or autophagia, oxidation. Cardiomyocyte hypertrophy refers to the enlargement of cardiomyocytes, with an increment in the content of intracellular proteins, especially those associated with contractile machinery, and with reexpression of fetal proteins such as the β-myosin heavy chain (β-MHC), and the auricular natriuretic factor (ANF). Cardiomyocyte hypertrophy is associated with cardiac hypertrophy. Cardiac hypertrophy refers to the enlargement observed in the hearts of high competition athletes (physiological or benign hypertrophy) or in individuals with hypertension post-myocardial infarction (pathological hypertrophy). Neointimal formation refers to the formation of undifferentiated new tissue or different type of tissue in blood vessels due to damage or any other cause including restenosis. Restenosis refers to renarrowing of any blood vessel, for example, renarrowing of a coronary artery after angioplasty. Restenosis can be caused by a number of other pathologies and causes. Fibroblast hyperplasia refers to an increment in the number of fibroblasts due to an increment in proliferation. Smooth muscle cell hyperplasia refers to an increment in the number of smooth muscle cell due to an increment in proliferation. Cytoprotection is understood as every phenomenon, process or mechanism involved in damage reduction or cell death reduction. Fibrosis is understood as an increment of tissue extracellular matrix content due to accumulation of proteins such as collagen, fibronectin, elastin, and the like. Apoptosis, necrosis, and autophagia refer to different types of cell death. Oxidative stress is understood as an increment of reactive oxygen species and it is caused by an unbalance between reactive oxygen species synthesis and degradation. Reactive oxygen species comprise superoxide anion ($O_2.^-$), hydrogen peroxide ($H_2O_2$), hydroxil radical (OH.) and/or products of these species with other molecules generating, for example, peroxynitrite (NOO.). The synthesis of reactive oxygen species can be achieved in the mitochondrial oxygen transport chain, NADPH oxidase, xhantin oxidase, NO synthase, by inorganic reactions such as Fenton's reaction, and Haber-Fenton's reactions, and the like. Mechanisms of degradation of reactive oxygen species include natural antioxidants (eg., vitamin C, alpha tocopherol, uric acid, mannitol), and enzymatic systems (eg., superoxide dismutase, catalase, glutation peroxidase, and the like). In this invention, the terms hypertrophy, neointimal formation, restenosis, hyperplasia, cytoprotection, fibrosis, collagen deposit, inflammation, oxidative stress, apoptosis, necrosis and autophagia must be understood in the broadest possible manner.

An effective amount refers to the dosage and period of time required to achieve the desired therapeutical outcome, that is, preventing, reverting, inhibiting, and/or reducing cardiovascular, pulmonary, renal, and/or cerebral remodeling. The effective amount may depend on several factors, such as, status and progression of the disease, age, gender, patient's weight, concurrent illnesses, concurrent medicaments, race, and the like. In this patent, the invention aims at elevating plasma and/or tissue angiotensin-(1-9) concentration to values above 10 fmol/g, more specifically to values above 20 fmol/g, even more specifically, to values above 40 fmol/g, still more specifically, to values above 80 fmol/g.

An angiotensin-(1-9) derivative refers to any mutation, fragment, part, or portion of angiotensin-(1-9) including molecules with substitution, deletion, and/or insertion of one or more angiotensin-(1-9) amino acids to mimic its biological and/or physiological effect, potentiate its biological and/or physiological effect, elevate its biological and/or physiological effect, increment its bioavailability, increment its stability, increment its absorption, increment its plasma and/or tissue half life, alter its plasma protein binding, increase its receptor affinity, reduce its degradation, or any other biological, physiological, pharmacological, and/or pharmaceutical property desired to enhance its therapeutic action. Angiotensin-(1-9) derivatives obtained by amino acid substitution refer to an amino acid substituted by other amino acid or by other molecule that may correspond to an amino acid derivative. In this case, a derivative functionally, structurally or esterochemically similar or homologous to angiotensin-(1-9) is desired. An angiotensin-(1-9) derivative also includes mimotopes, or peptides, or mimetic analogs, and include molecules containing non natural amino acids as well as molecules not related to amino acid but nevertheless their behaviour, functions and/or activities are similar to amino acids. Angiotensin-(1-9) derivatives also include modifications like glycosilations, amidations, acetylations, hydroxylations, methylations, ethylations, estheriphications, and the like, which are generally modifications of amino acid lateral chains or molecules contained within angiotensin-(1-9) or derivatives thereof. The introduction of crosslinking molecules which allow this peptide to bind to a larger structure which in turn helps with its physiochemical and/or pharmaceutical properties are considered as part of the angiotensin-(1-9) derivatives. The crosslinking molecules may have different chain lengths so that the angiotensin-(1-9) or derivatives thereof can be moved closer or further from the larger molecule. Crosslinkers may be homo- or bifunctional, such as bifunctional imido esters having a methyl group as spacer-chain length between n=1 and 6, glutaraldeheyde, N-hydroxysuccinimide esters, and heterobifunctional reactives which generally contain an amino reactive part such as the N-hydroxysuccinimide and another part which is specifically reactive to other or to the same functional group. Angiotensin-(1-9) derivatives also relates to chemically modified derivatives which help in 3D structure stabilization to make it easier to mimic its biological and/or physiological effect, potentiate its biological and/or physiological effect, elevate its biological and/or physiological effect, increase its bioavailability, increase its stability, increase its absorption, increase its plasma and/or tissue half life, alter its plasma protein binding, increase its receptor affinity, reduce its degradation, or any other biological, physiological, pharmacological, and/or pharmaceutical property desired to improve its therapeutic action.

Examples of non conventional or non-natural amino acids and/or their derivatives which may be introduced during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglicine, ornithine, sarcosine, 4-amino-3-hydroxy-6-methylheptanoico acid, 2-thienyl alanine and/or D-isomers of amino acids. Other examples of non-conventional or non-natural amino acids and/or their derivatives are: α-amino-α-methyl-butyrate, cyclopentylalanine, aminocyclopropane-carboxilic acid, cyclohexylalanine, aminoisobutyric acid, ácido aminonorbornyl-carboxilic acid, D-alanine, D-arginine, D-aspartic acid, D-cysteine, D-glutamine, D-glutamic acid, D-histidine, D-isoleucine, D-leucine, D-lysine, D-methionine, D-ornithine, D-phenylalanine, D-proline, L-N-methylalanine, L-N-methylarginine, L-N-methylasparagine, L-N-methylaspartic acid, L-N-methylcysteine, L-N-methylglutamine, L-N-methylglutamic acid, cyclohexyl L-N-methylhistidine, L-N-methylisolleucine, L-N-methylleucine, L-N-methyllisine, L-N-methylmethionine, L-N-methylnorleucine, L-N-methylnorvaline, L-N-methylornithine, L-N-methylphenylalanine, L-N-methylproline, L-N-methylserine, L-N-methylthreonine, L-N-methyltryptophan, L-N-methyltyrosine, L-N-methylvaline, L-N-methylethylglycine, D-serine, D-threonine, D-tryptophan, D-tyrosine, D-valine, D-α-methylalanine, D-α-methylarginine, D-α-methylasparagine, D-α-methylaspartate, D-α-methylcysteine, D-α-methylglutamine, D-α-methylhistidine, D-α-methylisoleucine, D-α-methylleucine, D-α-methyllysine, D-α-methylmethionine, D-α-methylornithine, D-α-methylphenyl-alanine, D-α-methylproline, D-α-methylserine, D-α-methylthreonine, D-α-methyltryptophan, D-α-methyltyrosine, D-α-methylvaline, D-N-methylalanine, D-N-methylarginine, D-N-methylasparagine, D-N-methylaspartate, D-N-methylcysteine, D-N-methylglutamine, D-N-methylglutamate, D-N-methylhistidine, D-N-methylisoleucine, D-N-methylleucine, L-N-methyl-t-butylglicine, L-norleucine, L-norvaline, α-methyl-aminoiso-butyrate, α-methyl-α-amino-butyrate, α-methylcyclohexyl-alanine, α-methylcylcopentyl-alanine, α-methyl-α-napthyl-alanine, α-methylpenicillamine, N-(4-aminobutyl)glycine, N-(2-aminoethyl)glicine, N-(3-aminopropyl)glicine, N-amino-α-methyl-butyrate, α-napthylalanine, N-benzylglycine, N-(2-carbamylethyl)glycine, N-(carbamylmethyl)glycine, N-(2-carboxyethyl)glycine, N-(carboximethyl)glycine, N-cyclobutylglycine, N-cycloheptylglycine, N-cyclohexylglycine, N-cyclodecylglycine, N-cyclododecylglycine, N-cyclooctylglycine, N-cyclopropylglycine, N-cycloundecylglycine, N-(2,2-diphenylethyl)glycine, N-(3,3-diphenylpropyl) glycine, N-(3-guanidinopropyl)glycine, N-(1-hydroxyethyl) glycine, N-(hydroxyethyl)glycine, N-(imidazolylethyl)) glycine, N-(3-indolyliethyl)glycine, D-N-methyllysine, N-methylcyclohexylalanine, D-N-methylornithine, N-methylglycine, N-methylaminoisobutyrate, N-(1-methylpropyl) glycine, N-(2-methylpropyl)glycine, D-N-methyltryptophan, D-N-methylthyrosine, D-N-methylvaline, α-aminobutyric acid, L-t-butylglycine, L-ethylglycine, L-homophenylalanine, L-methylarginine, L-methylaspartate, L-methylcysteine, L-methylglutamine, L-methylhistidine, L-methylisoleucine, L-methylleucine, L-methylmethionine, L-methylnorvaline, L-methylphenylalanine, L-methylserine, L-methyltryptophan, L-methylvaline, N—(N-(2,2-diphenylethyl) carbamylmethyl)glycine, 1-carboxi-1-(2,2-diphenylethylamino)cyclopropane, N-methyl-α-amino-butyrate, D-N-methylmethionine, N-methylcyclopentylalanine, D-N-methylphenylalanine, D-N-methylproline, D-N-methylserine, D-N-methylthreonine, N-(1-methylethyl)glycine, N-methyl-α-naphthyl-alanine, N-methylpenicillamine, N-(p-hydroxyphenyl)-glycine, N-(thiomethyl)glycine, penicillamine, L-α-methylalanine, L-α-methylasparagine, L-α-methyl-t-butyl-glycine, L-methylethylglycine, L-α-methylglutamate, L-α-methylhomophenyl-alanine, N-(2-methylthioethyl)glycine, L-α-methyllysine, L-α-methylnorleucine, L-α-methylornithine, L-α-methylproline, L-α-methylthreonine, L-α-methyltyrosine, L-N-methylhomophenylalanine, and N—(N-(3,3-diphenyl-propyl) carbamylmethyl)glycine.

As described above, an angiotensin-(1-9) chemical analogue and/or homologue share certain conformational and/or functional similarities, but it is not necessarily derived from angiotensin-(1-9). Thus, a chemical equivalent may be designed to mimic certain biological and/or physiological properties of angiotensin-(1-9).

Although the present invention is particularly exemplified herein in relation to the use of angiotensin-(1-9) and/or derivatives thereof and medicaments, or pharmaceutical compositions thereof in rats, it is understood that the present invention extends to the use of the angiotensin-(1-9) and/or derivatives thereof and medicaments, or pharmaceutical compositions thereof according to the invention in any mammal including, but not limited to, humans, mice, rabbits, primates, dogs, cats, pets, livestock animals, etc.

EXAMPLES

Example 1

Experimental Design in Animals

Male Sprague Dawley rats were kept in cages with access to water and food ad libitum. This procedure was performed in accordance with the Guide for the Care and Use of Laboratory Animals, published by "U.S. National Institutes of Health" (NIH publication No 85-23, revised 1985) and was approved by our Institutional Ethics Committee. For studies with enalapril and candesartan, 71 adult normotensive rats were randomly separated into two groups and underwent a sham surgery (surgery without ligation of the coronary artery, n=34) or myocardial infarction following a surgery with ligation of the left coronary artery (infarction, n=37) as previously described (Ocaranza et al, Hypertension 48:572-8, 2006). Briefly, the left coronary artery was ligated between the pulmonary artery exit and left auricle with a 7-0 silk suture under aseptic conditions in rats anaesthetized with ketamine-HCl/xilazine (35/7 mg/kg intraperitoneal, respectively). Sham rats underwent the same surgical procedure except that the suture was not passed around the left coronary artery. Myocardial infarction was confirmed by electrocardiography 24 h following surgery. Mortality rate from myocardial infarction following ligation of the left coronary artery was 25% within 48 h after occlusion. Infarct size in survivors was determined by planimetry of endocardial circumference of left ventricle on histological sections. Sham and infracted rats were randomized to receive the carrier, candesartan (10 mg/kg of body weight daily) or enalapril (10 mg/kg of body weight daily) by gavage for 8 weeks, beginning 48 h after infarction.

For studies with angiotensin-(1-9) 28 rats were randomly distributed into two groups and underwent a sham surgery (n=8) or infarction following left coronary artery ligation (n=20). The infarcted rats were randomized to receive the either the carrier, angiotensin-(1-9) (463 ng/kg of body weight for 14 days) or angiotensin-(1-9) plus A779 (463 ng of angiotensin-(1-9)/kg of body weight/min and 100 ng of A779/kg/min for 14 days) by means of osmotic mini-pumps (ALZET) implanted into the jugular under sedation with ketamine-HCl/xilazine (35/7 mg/kg intraperitoneal, respectively).

Example 2

Hemodynamic and Functional Assays

Systolic blood pressure (SBP) was determined by using the "tail-cuff" method by investigators who were blind to the treatment group. Left ventricle function was determined by transthoracic bidimensional echocardiography using a Sonos 5000 equipped with a 5 to 12 MHz sectorial electronic ultraband S12 Philips transducer. The following echocardiographic parameters were determined: left ventricular end-systolic diameter (LVESD), left ventricular end diastolic diameter (LVEDD), left ventricular fractional shortening (LVFS), left ventricular anterior wall thickness (LVAWT), and left ventricular posterior wall thickness (LLVWT).

Example 3

Cardiovascular, Renal, Pulmonary, or Cerebral Remodeling Assessment

Cardiovascular, pulmonary, renal, and cerebral remodeling was determined on histological sections of collagen-containing tissue, fibroblast contents, cellular proliferation rate, macrophage infiltration (inflammation), and levels of cell death (apoptosis, necrosis and autophagia). In case of cardiac remodeling, cardiac hypertrophy, cardiac morphologic and morphometric assessment were also determined. In the case of blood vessel remodeling, blood vessel hypertrophy was also determined.

Cardiac Hypertrophy Assessment

The extent of left ventricular hypertrophy was calculated by the relationship among left ventricular weight (LVW), body weight (BW), mRNA relative levels of the auricular natriuretic factor (ANF), left ventricular protein content (LVP), and protein levels of β-myosinheavy chain (β-MHC) as described in (Ocaranza et al, Hypertension 48:572-8, 2006).

Cardiac Tissue Morphologic and Morphometric Assessment

Heart mid-ventricle transverse slices (10 μm) were embedded in paraffin, stained with hematoxylin and eosin, and were examined by light microcopy (×20). The size of cardiomyocytes was determined as described by Nakamura et al (Circulation 98:794-9, 1998). Briefly, cell images visualized on a video recorded attached to the microscope were projected in a monitor and they were plotted. The area and perimeter were determined using Image J. software. All measurements were made by a blind observer. At least 70 cells per animal were measured.

Blood Vessel Hypertrophy Assessment

The technique as described by Igase et al was followed (Am. J. Physiol. 289:H1013-9, 2005). Briefly, medial and lumen areas were determined by measuring the length of the internal elastic lamina (IEL) and the length of the external elastic lamina (EEL) through digitalized images. Pixel values between laminae were converted into area by calculating their ratio. Medial area was obtained by IEL-EEL. Lumen area was represented by IEL limited area. Lumen-medial ratio was calculated from lumen area/medial area ratio. Medial thickness was calculated by (EEL diameter–IEL diameter)/2.

Collagen Content Assessment

Collagen was determined by performing a morphometric analysis of collagen. 5 μm thickness sections of left ventricle, kidney, blood vessel, and/or brain were cut and stained with picrosirius red, as described by Jalil et al (Circ. Res. 64:1041-50, 1989). Cuts were observed through a light microscope connected to a computer, where images were obtained by Video Player program with a 200× enlargement, and the result was calculated semi-automatically by a software made at our laboratory in Math Lab, previously validated (Ocaranza et al, J. Cardiovasc. Pharmacol. 40:246-54, 2002).

Fibroblast Content Assessment and Cellular Proliferation Determination

Blood vessels, kidney, lungs, brain, and/or heart were dehydrated at room temperature and embedded in paraffin. Sections of 5 μm were immunostained with antinuclear Ki-67 cell proliferation antigen antibodies (Ocaranza et al, Am. J. Physiol. 286:H498-506, 2004). For determination of positive-stained cell type, serial sections were cut followed by staining with antivimentin antibodies (fibroblasts), anti skeletal α-actin (SKA, myocytes), anti Von Willebrand factor (endothelial cells), and anti-vimentin, anti-smooth muscle α-actin (smooth muscle cells). For reaction detection, peroxidase-conjugated biotinylated antibodies and cut sections were counterstained with hematoxylin.

Assessment of Cytoprotecton, Apoptosis, Necrosis, and Autophagia

Apoptosis was determined by DNA fragmentation. This was performed by the TUNEL technique and by purified DNA on 2% agarose gel analysis. Procedures as described by (Galvez et al, Cell Tissue Res. 304:279-85, 2001; Ibe et al Eur. J. Heart Fail. 9:160-7, 2007) were used. Increased apoptosis was evidenced by a higher number of stained cells (positive) under microscope using the TUNEL technique, whereas on agarose gels an increased amount of DNA fragments (between 200 and 1000 bp) than in controls was observed. Necrosis was determined by the release of lactate dehydrogenase into extracellular medium (Parra et al, Cardiovasc. Res. 77:387-97, 2008). Autophagia was determined by LC3 protein fragmentation and by the presence of autophagic vesicles (Wohlgemuth et al, Rejuvenation Res. 10:281-92, 2007). Cytoprotection was determined by morphometric analysis of eosin-stained tissues, and visualized by light microscopy.

Inflammation Assessment

Blood vessels, kidney, lungs, brain, and/or heart were dehydrated at room temperature and embedded in paraffin. Sections of 5 µm were immunostained with anti-ED-1 antibodies, a macrophage/monocyte marker. At the same time, MCP-1 mRNA levels in different tissues were determined. RNA was isolated by TRIZOL method and concentration and purity was determined by UV spectrometry. RNA integrity was assessed by 18 and 28S rRNA bands. MCP-1 mRNAs levels were calculated by RT-PCR (Ocaranza et al, Hypertension 48:572-8, 2006).

Example 4

Level Determination of mRNA, Angiotensin I-Converting Enzyme Protein (ECA), and Homologous Angiotensin I-Converting Enzyme (ECA-2)

Total RNA (1.5 µg) of a non infarcted left ventricle area was isolated using Trizol reactive and treated with DNAase, and it was quantified through UV spectroscopy. Reverse transcriptase reaction coupled with chain polymerization reaction (RT-PCR) was performed using ACE and ACE-2 primers, already described (Ocaranza et al, Hypertension 48:572-8, 2006). cDNA amplification conditions for CEA-2 were already described by (Ocaranza et al, Hypertension 48:572-8, 2006). After PCR, amplification products were fractioned on 1.5% agarose gels (w/w) and visualized by ethidium bromide staining. Band intensities were quantified through densitometry and were normalized with regard to RNA 18S.

Expression of ACE and ACE-2 Proteins

Ventricle samples were treated with 4% formalin, fixed for 24 h, embedded in paraffin and cut in 5 µm sections. Sections were immunodetected for ACE with a IgG monoclonal antibody (1/100, Chemicon) or ACE-2 with a polyclonal antibody (1/500, Millenium Pharmaceuticals) and with anti-mouse or anti-rabbit IgG biotinylated antibody (Dako). Sections develop using fuchsin (Dako) such as chromogen, counterstained with hematoxylin, and assessed by microscopy.

Example 5

Determination of Plasma Angiotensin and Bradykinin Levels

Plasma angiotensin and bradykinin levels were determined as described by (Ocaranza et al, Hypertension 48:572-8, 2006; Ocaranza et al, Life Sci. 78:1535-42, 2005; Campbell et al, J. Mol. Cell. Cardiol. 27:1545-60, 1995). Briefly, rats were anesthetized with a combination of ketamin (125 mg/kg) and xilazin (12.5 mg/kg) administered via intraperitoneal injection. Blood was drawn from the inferior vena cava directly into a syringe containing 5 mL of 4 M guanidinium isothiocyanate using a 25G needle. Plasmas were stored at −80° C. until their extraction using C18 Sep-Pak cartridges, and peptides were acetylated. Acetylated angiotensin II, angiotensin I, angiotensin-(1-7), angiotensin-(1-9), bradykinin-(1-7) and bradykinin-(1-9) were separated by high performance liquid chromatography (HPLC) and were detected by radioimmunoassay.

Example 6

Hypertrophy of Cultured Cardiomyocytes

Assay Conditions

Neonatal Sprague-Dawly rat cardiomyocytes were isolated as described by (Foncea et al, J. Biol. Chem. 272:19115-24, 1997). Every study is in accordance with the guide for the care and use of laboratory animals Published by "U.S. National Institutes of Health" (NIH publication No 85-23, revised 1985) and was approved by our Institutional Ethics Committee. Cell cultures were >95% pure. Cardiomyocytes were plated at 70% final density in gelatin coated plates and kept at 37° C. in a 5% $CO_2$/95% air moisturized atmosphere for 24 h in DMEM/M199 (4:1) with 10% bovine fetal serum and 5% calf serum. Serum was removed 24 h before cell were preincubated with 10 or 100 µM angiotensin-(1-9) for 1 h before incubation with 100 µM norepinephrine (Sigma) or 10 nM IGF-1 (Austral Biological) for 24 h.

Sarcomerization Assays and Cardiomyocyte Size Determination

Cells were grown over slides and were incubated in a buffer conferring stability to the cytoskeleton (10 mM MES pH 6.0, 150 mM NaCl, 5 mM EDTA, 3% sucrose, 5 mM $MgCl_2$) for 5 min. Then, cells were fixed and permeabilized using methanol for 10 min. Non specific binding sites were blocked for 1 h with phosphate-buffered saline (PBS) supplemented with 3% bovine serum albumin. Cardiomyocytes were washed with PBS and incubated at room temperature for 45 min with phalloidine-rhodamine 1:400 (for F-actin staining, red). Slides were washed and mounted on "DakoCytomation Fluorescent Mounting Medium". Cellular staining was evaluated in a confocal microscope (Carl Zeiss Axiovert 135, LSM Microsystems). Cardiomyocyte size was determined in cells fixed with 4% paraformaldehyde for 10 min and permeabilized with methanol for 10 min. Cells were then incubated overnight at room temperature with an anti-β-MHC antibody (1:80). The size of at least 100 cells from randomly selected fields was determined using Image J (NIH) software.

Example 7

Production of Viral Vectors that Overexpress the Homologous Angiotensin I-Converting Enzyme (ECA-2)

Production of an Adenovirus that Overexpresses the Homologous Angiotensin I-Converting Enzyme ACE2 gene was initially subcloned (Genebank human access code: NM_021804; Genebank rat access code: NM_001012006) into the adenoviral plasmid pDC316 (Microbix Byosystem Inc). Positive clones were confirmed by sequencing. Later, plasmid pDC316 containing the ACE2 gene was cotransfected with the adenoviral plasmid pBH-Glox(delta)E1,3Cre in HEK293 cells. The recombinant adenovirus was obtained by homologous recombination between two plasmid as described by Hardy et al (J. Virol. 71:1842-9, 1997). Confirmation that the produced adenovirus overexpressed ACE2 was carried out by neonatal rat cardiomyocyte transduction in culture with multiplicity of infections (MOI) with adenovirus expressing ACE2. ACE2 overexpression was verified by determination of ACE2 protein levels by Western blot and by ACE2 enzymatic activity. FIG. 1 depicts the ACE 2 overexpression in cultured cardiomyocytes using different multiplicity of infection (MOI) with an adenovirus overexpressing ACE-2. At base level, it is not possible to detect the presence of ACE2 in cultured cardiomyocytes, however, by ACE2 expression using an adenovirus it is possible to elevate ACE-2 levels several hundred times (FIG. 1).

Production of a Lentivirus Overexpressing the Homologous Angiotensin I-Converting Enzyme ACE2 gene was initially subcloned (human=Genebank access code: NM_021804; rat=Genebank access code: NM_001012006) into the lentiviral plasmid PHAGE-PGK. Lentiviruses were produced in HEK293T cells by simultaneous cotransfection of the lentiviral vector containing ACE 2 cDNA and vectors pCMVdeltaR8.9 and pHCMV-G according to the procedure described by Zufferey et al (J Virol. 72:9873-80, 1998). Confirmation that the produced lentivirus overexpressed ACE2 was performed by cultured neonatal rat cardiomyocytes with different multiplicity of infections (MOI) with the lentivirus expressing ACE2. ACE2 overexpression was verified through determination of ACE2 protein levels by Western Blot, and by ACE2 enzymatic activity.

Production of a Retrovirus Overexpressing the Homologous Angiotensin I-Converting Enzyme ACE2 gene was initially subcloned (human=Genebank access code: NM_021804; rat=Genebank access code: NM_001012006) into the retroviral plasmid pCnBgSN (or any other retroviral plasmid). Retroviruses were produced from HEK293T cells by simultaneous cotransfection of retroviral vector containing ACE2 cDNA and vectors pHIT60 (for gal-pol) and pCVG (for VSV-G) according to the procedures described by Yu & Kwon (Methods in Molecular Biology, vol. 433: Volume 1: Production and In Vivo Applications, Edited by: J. M. Le Doux© Humana Press, Totowa, N.J., pages 1-16). Confirmation that the produced retrovirus overexpressed ACE2 was performed by transduction of cultured neonatal rat cardiomyocytes with different multiplicity of infection (MOI) with the retrovirus expressing ACE2. ACE2 overexpression was verified by determining ACE2 protein levels by Western blot and by ACE2 enzymatic activity.

Production of an Adeno-Associated Virus Overexpressing the Homologous Angiotensin I-Converting Enzyme ACE2 gene was initially subcloned (human=Genebank access code: NM_021804; rat=Genebank access code: NM_001012006) into the plasmid of the adeno-associated virus pAAV-MCS (Stratagene). Adeno-associated viruses were produced from HEK293T cells by simultaneous cotransfection of the adeno-associated virus vector containing ACE2 cDNA and vectors pAAV-RC (pAAV-helper or pRC, containing genes rep and cap), and pAdV-Helper (or pHelper, which carries genes E2A, E4 and VA-RNAs) according to the procedure described by Stratagene. Confirmation that the produced adeno-associated virus overexpressed ACE2 was performed by transduction of cultured neonatal rat cardiomyocytes with different multiplicities of infection (MOI) with the adeno-associated virus expressing ACE2. ACE2 overexpression was verified by determining ACE2 protein levels by Western blot and by ACE2 enzymatic activity.

Example 8

Intracardiac and Blood Vessel Administration of Viral Vectors Overexpressing Homologous Angiotensin I-Converting Enzyme (Ace-2)

The infections in animals were performed according to the technique described by Coleman et al (Physiol Genomics 12:221-8, 2003). Briefly, male rats of 150±10 g of weight were anesthetized with ketamin and xilazin at doses of 50 mg/Kg/weight and 10 mg/Kg/weight respectively, via intraperitoneal route, followed by intubation via the larynx inserting a 18-gauge soft catheter and was ventilated with a tidal volume of approximately 2 mL to 60 cycles/min (SAR-830 small animal mechanical ventilator). A toracotomy was performed at the level of the left intercostal fifth space, and a 24-gauge catheter with 30 µL of adenoviral, lentiviral or sterile adeno-associated virus solution was introduced into the left ventricular chamber. After inserting the drainage tube to remove air and blood, the incision was closed; animals were allowed to recover and were returned to their respective cages. Mortality rate after this surgery was around 20% and it has been established for myocardial tissue long term gene transfer (for details see Methods in Molecular Biology, vol. 219: Cardiac Cell and Gene Transfer, Edited by: J. M. Metzger© Humana Press Inc., Totowa, N.J.).

Example 9

Effect of Angiotensin-(1-9) Administration on Hemodynamic Parameters

Continuous administration of angiotensin-(1-9) through osmotic mini-pumps (ALZET) (see example 1) does not alter blood pressure in treated animals (table 1). However, a significant reduction of the left ventricle weight (LVW) is observed (table 1).

TABLE 1

Effects of angiotensin-(1-9) administration on hemodynamic parameters.

| Parameter | S | MI | MI-Ang-(1-9) | MI-Ang-(1-9)-A779 |
|---|---|---|---|---|
| N | 8 | 8 | 6 | 6 |
| BW (g) | 255 ± 6 | 264 ± 6 | 274 ± 24 | 277 ± 4 |
| SBP (mm Hg) | 115 ± 4 | 110 ± 3 | 112 ± 2 | 117 ± 9 |
| LVW (mg) | 830 ± 20 | 910 ± 20* | 810 ± 7# | 823 ± 31# |
| LVW/BW (MV/100 g BW) | 325 ± 9 | 355 ± 10* | 310 ± 16# | 305 ± 19# |
| CPVI (mg) | 8.2 ± 0.14 | 9.8 ± 0.3* | 8.0 ± 0.3# | 8.4 ± 0.2# |
| FC (beats/min) | 276 ± 14 | 271 ± 7 | 259 ± 14 | 260 ± 10 |

Values are average ± SEM.

Abbreviations: MI: myocardial infarction; N: number of animals; BW: body weight; SBP: systolic blood pressure, LVW: left ventricle weight; HR: heart rate.

*$p < 0.05$ vs sham,

$p < 0.05$ vs MI (after a significant ANOVA).

Example 10

The Anti-Remodeling Effects of Converting Enzyme 1 (CEA) Inhibitor and Angiotensin II Receptor Antagonist (AT1) are Mediated by Increased Angiotensin-(1-9) Levels In order to demonstrate that angiotensin-(1-9) is involved in the pharmacological effects of cardiovascular drugs acting on the renin-angiotensin system, and that this peptide is a new antihypertrophic factor, we compared the effects of the classic ACE inhibitor enalpril with those obtained with AT1 receptor antagonist candesartan on a myocardial infarction model. Left ventricular hypertrophy (LVH) was assessed by ecocardiography, relative left ventricle weight (RLVW, mg left ventricle weight (LVW)/body weight (BW)), relative levels of auricular natriuretic factor (ANF) mRNA, left ventricle protein (LVP) content, and β-myosin heavy chain (β-MHC) content are described in example 1.

Infarct mean size was similar in all infracted treated and non-treated rats. Four hypertrophy markers (LVW/BW ratio, LVP content, ANF mRNA de and β-MHC levels) increased significantly at week 8 after descending coronary artery ligation, and were reduced by candesartan or enalapril administration. Both drugs significantly prevented left ventricle dilatation, whereas only candesartan reduced the left ventricle wall thickness (LLVWT) in infarcted rats (Table 2).

TABLE 2

Effect of AT1 receptor angiotensin candesartan and ACE inhibitor enalapril on blood pressure, morphometry, and function of the left ventricle induced by coronary artery ligation.

| Parameter | S | MI | C-S | C-MI | E-S | E-MI |
|---|---|---|---|---|---|---|
| N | 11 | 12 | 13 | 13 | 10 | 12 |
| BW (g) | 380 ± 8 | 372 ± 10 | 343 ± 11*# | 357 ± 10*# | 350 ± 7*# | 345 ± 4*# |
| SBP (mm Hg) | 123 ± 2 | 117 ± 2 | 84 ± 4*#¶ | 88 ± 4*#¶ | 113 ± 2*# | 110 ± 3*# |
| Infarct size LV (%) | NA | 29 ± 1 | NA | 30 ± 1 | NA | 31 ± 2 |
| LVW/BW (mg/g) | 3.0 ± 0.1 | 3.6 ± 0.1* | 2.7 ± 0.1*# | 2.8 ± 0.1*# | 2.7 ± 0.2* | 2.9 ± 0.3*# |
| mRNA ANF (times) | 1.0 ± 0.1 | 1.7 ± 0.2* | 0.7 ± 0.2 | 1.1 ± 0.2*¶ | 0.9 ± 0.1 | 1.6 ± 0.1 |
| LVP content (mg) | 11.1 ± 0.3 | 30.1 ± 3.3* | 11.6 ± 1.1 | 12.3 ± 1.4# | 12.4 ± 0.8 | 12.8 ± 0.5# |
| β-MHC (times) | 1.0 ± 0.2 | 2.2 ± 0.2* | 1.1 ± 0.2 | 1.0 ± 0.1# | 1.3 ± 0.2 | 1.2 ± 0.1# |
| LVESD (mm) | 5.2 ± 0.1 | 6.9 ± 0.3* | 5.1 ± 0.1 | 5.9 ± 0.4# | 5.2 ± 0.1 | 5.4 ± 0.3# |
| LVEDD (mm) | 7.4 ± 0.2 | 8.8 ± 0.2* | 7.7 ± 0.2 | 8.0 ± 0.3# | 7.5 ± 0.3 | 7.1 ± 0.2# |
| LVFS (%) | 29 ± 2 | 22 ± 3* | 30 ± 2 | 22 ± 2* | 30 ± 1 | 21 ± 1* |
| LVAWT (mm) | 1.5 ± 0.1 | 1.0 ± 0.1* | 1.1 ± 0.4 | 0.9 ± 0.4* | 1.3 ± 0.2 | 0.9 ± 0.1* |
| LLVWT (mm) | 1.4 ± 0.1 | 1.6 ± 0.1* | 1.1 ± 0.0 | 1.2 ± 0.0*# | 1.4 ± 0.0 | 1.5 ± 0.1 |

Values are average ± SEM.
Abbreviations: S: sham; MI: myocardial infarction; C: candesartan; E: enalapril; N: number of animals; BW: body weight; SBP: systolic blood pressure; LVW: left ventricle weight; ANF: auricular natriuretic factor; LVP: left ventricle protein content; β-MHC: β-myosin heavy chain; LVESD: left ventricular end-systolic diameter; LVEDD: left ventricular end-diastolic diameter; LVFS: left ventricle fractional shortening; LVAWT: left ventricular anterior infarcted wall thickness; LLVWT: left ventricular posterior infarcted wall thickness; NA: not applicable.
*p < 0.05 vs S;
p < 0.05 vs MI,
¶p < 0.05 vs E-MI (after a significant ANOVA).

Plasma angiotensin and bradykinin (BK) levels were determined by high performance liquid chromatography and radioimmunoassay as described in example No 2. Angiotensin-I levels are lower in the infarcted rats group, associated with higher levels of angiotensin-II. However, plasma angiotensin-(1-7) and angiotensin-(1,9) levels were similar in sham rats and infarcted rats. Enalapril and candesartan increase both angiotensin-(1-9) circulating levels, and -(1-7)/angiotensin-II and angiotensin-(1-9)/angiotensin-I ratios in both experimental groups. Plasma angiotensin-(1-7) levels were increased by candesartan, and bradykinin-(1-9) levels were increased by enalapril both in infarcted rats and sham rats (Tables 3 and 4).

TABLE 3

Effects of AT1 receptor antagonist candesartan and ACE inhibitor on circulating levels of angiotensin-I, angiotensin-II, angiotensin-(1-7) and angiotensin-(1-9) post coronary artery ligation.

| Parameter | S | MI | C-S | C-MI | E-S | E-MI |
|---|---|---|---|---|---|---|
| N | 10 | 9 | 12 | 11 | 10 | 10 |
| Ang I (fmol/g) | 29.8 ± 4.0 | 13.1 ± 1.6* | 22.6 ± 5.3 | 30.7 ± 1.9# | 30.7 ± 1.0 | 32.4 ± 0.8# |
| Ang-(1-7) (fmol/g) | 4.3 ± 1.1 | 2.9 ± 0.5 | 10.9 ± 1.6*#¶ | 14.4 ± 2.7*#¶ | 4.1 ± 0.5 | 3.8 ± 0.6 |
| Ang-(1-9) (fmol/g) | 5.3 ± 0.8 | 5.7 ± 0.9 | 36.2 ± 4.1*# | 43.8 ± 2.9 *#¶ | 25 ± 5* | 29 ± 3*# |
| Ang II (fmol/g) | 24.3 ± 3.0 | 33.0 ± 2.5* | 38.6 ± 7.2* | 34.6 ± 4.2*¶ | 15.4 ± 3.8* | 23.3 ± 5.4# |
| Ang II/Ang I | 0.86 ± 0.08 | 2.83 ± 0.11* | 3.3 ± 0.9* | 4.5 ± 0.6*#¶ | 0.45 ± 0.05* | 0.72 ± 0.1*# |

TABLE 3-continued

Effects of AT1 receptor antagonist candesartan and ACE inhibitor on circulating levels of angiotensin-I, angiotensin-II, angiotensin-(1-7) and angiotensin-(1-9) post coronary artery ligation.

| Parameter | S | MI | C-S | C-MI | E-S | E-MI |
|---|---|---|---|---|---|---|
| Ang-(1-9)/Ang I | 0.18 ± 0.02 | 0.42 ± 0.06* | 2.6 ± 0.7* | 2.8 ± 1.1*#¶ | 0.75 ± 0.03* | 0.89 ± 0.02*# |
| Ang-(1-7)/Ang II | 0.16 ± 0.02 | 0.10 ± 0.01* | 0.49 ± 0.15* | 1.02 ± 0.06*#¶ | 0.25 ± 0.07 | 0.26 ± 0.02*# |

Values are average ± SEM.
Abbreviations: S: sham; MI: myocardial infarction; C: Candesartan; E: enalapril; N: number of animals; Ang: angiotensin.
*$p < 0.05$ vs S;
$p < 0.05$ vs MI;
¶$p < 0.05$ vs E-MI (after a significant ANOVA).

TABLE 4

Effects of AT1 receptor antagonist candesartan and ACE inhibitor enalapril on circulating levels of bradykinin-(1-7) and bradykinin-(1-9) post coronary artery ligation.

| Parameter | S | MI | C-S | C-MI | E-S | E-MI |
|---|---|---|---|---|---|---|
| N | 10 | 9 | 12 | 11 | 10 | 10 |
| Bk-(1-7) (fmol/g) | 3.16 ± 0.84 | 2.80 ± 0.54 | 4.41 ± 1.5 | 5.44 ± 1.60 | 1.48 ± 0.46*# | 1.40 ± 0.17*# |
| Bk-(1-9) (fmol/g) | 3.89 ± 1.12 | 4.25 ± 1.00 | 4.30 ± 1.36 | 4.08 ± 1.43¶ | 9.53 ± 2.99* | 7.89 ± 1.22*# |
| Bk-(1-7)/Bk-(1-9) | 1.09 ± 0.85 | 0.75 ± 0.42 | 1.69 ± 0.51 | 1.18 ± 0.21¶ | 0.19 ± 0.04*# | 0.17 ± 0.06*# |

Values correspond to media ± SEM.
Abbreviations: S: sham; MI: myocardial infarction; C: Candesartan; E: enalapril; N: number of animals; Bk: bradykinin.
*$p < 0.05$ vs S;
$p < 0.05$ vs MI;
¶$p < 0.05$ vs E-MI (after a significant ANOVA).

Among experimental groups, only plasma angiotensin-(1-9) levels but not angiotensin-II or angiotensin-(1-7) levels correlated significantly with LVH and protein levels (r=−0.35, F=8.44, p<0.01, n=62, r=−0.35, F=7.25, p<0.01, respectively, FIGS. 2a-b). These results indicate that both ACE inhibitor and AT1 receptor antagonist increase plasma angiotensin-(1-9) levels and that this effect was associated with a left ventricle hypertrophy and left ventricle remodeling attenuation.

Example 11

The Administration of Angiotensin-(1-9) Inhibits Remodeling

The effects of chronic administration of angiotensin-(1-9) for two weeks to rats with myocardial infarction via Alzet osmotic mini-pumps (see example 3) without observing changes in body weight, systolic blood pressure, or heart rate in experimental groups are now assessed (Table 4).

In these experiments, the area and perimeter of heart cardiomyocytes of sham rats, infarcted and infarcted and treated with angiotensin-(1-9) were determined (FIG. 3a-b). In infarcted rats, cellular area increased by 69% compared with sham rats (p<0.01), whereas angiotensin-(1-9) administration prevented cellular area increment compared with infracted rats (p<0.01, FIG. 3b). The cardiomyocyte perimeter followed the same tendency as the cellular area and increased by 28% in infarcted rats with regard to sham rats (p<0.01) and decreased by 31% through the administration of angiotensin-(1-9) with regard to infracted rats (p<0.01, FIG. 3b). Fetal genes are normally activated during embrionary development and are suppressed during adulthood. However, in pathological conditions, these genes are overexpressed and are traditionally considered as molecular markers of pathological cardiac hypertrophy (Schneider et al, Basic Res. Cardiol. 87 Suppl 2:33-48, 1992; van Bilsen & Chien, Cardiovasc. Res. 27:1140-9, 1993). Both the mRNA expression of the aurical natriuretic factor (ANF) and β-MHC protein levels were determined by RT-PCR and Western blot, respectively (see example 4). Infarcted rats exhibited a 310% increment in ANF mRNA levels compared with sham rats (p<0.01, FIG. 4a-b) and a reduction of 81% in infarcted rat treated with angiotensin-(1-9) compared with infracted rats (p<0.01, FIG. 4b). 13-MHC protein levels in left ventricle (FIG. 5a-b) increased by 90% in infarcted rats compared with sham rats (p<0.01, FIG. 5b) and decreased by 48% in infracted rats treated with angiotensin-(1-9) compared with infracted rats (p<0.01). As a whole, these results indicate that the administration of angiotensin-(1-9) prevents cardiac remodeling after myocardial infarction. Since angiotensin-(1-9) can be hydrolyzed by ACE to form angiotensin-(1-7), we have proven this hypothesis by co-administering A799, the antagonist described for angiotensin-(1-7) receptor (Lara et al, Regul. Pept. 103:17-22, 2002), with angiotensin-(1-9) to infarcted rats for two weeks. A799 did not modify the preventing effects of angiotensin-(1-9) on the increments of area and perimeter of cardiomyocytes induced after myocardial infarction (FIG. 3a). The effect of A779 was corroborated by measuring circulating levels of angiotensin-(1-7) in infarcted rats treated with angiotensin-(1-9) and A779, and in infracted rats treated with angiotensin-(1-9). A779 increased plasma angiotensin-(1-9) levels; the levels being 9.26±1.25 vs 6.8±0.8 fmols/g (rats with myocardial infarction and treated vs infracted rats not treated with A779, respectively, p<0.01). As a whole, this data indicates that the in vivo anti-remodeling effects of angiotensin-(1-9) on cardiac tissue are not mediated by angiotensin-(1-7).

Example 12

Angiotensin-(1-9) Inhibits Primary Cultured Cardiomyocyte Hypertrophy

Figure 6:
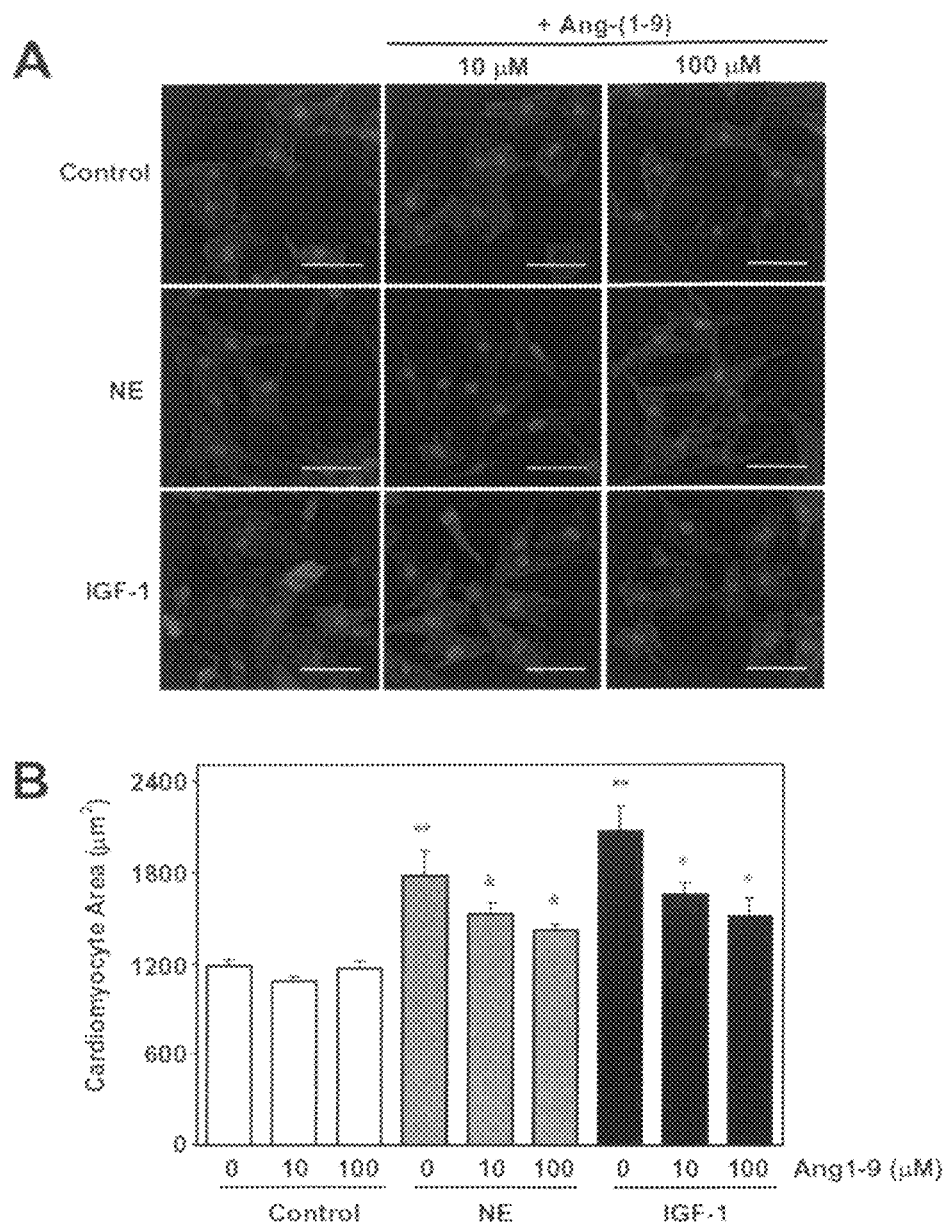

These in vivo anti-hypertrophic effects of angiotensin-(1-9) were confirmed by in vitro experiments using cultures of neonatal cardiomyocytes. Cultured cardiomyocyte hypertrophy was performed by administering norepinephrine (NE) and insulin-like growth factor 1 (IGF-1). As shown in FIG. 6, increments in cardiomyocyte areas induced by NE (10 μM) or IGF-1 (10 nM) were significantly prevented by the co-addition of 10 or 100 μM of angiotensin-(1-9). Similar effects were observed on cardiomyocyte perimeter and carcomerization with angiotensin-(1-9).

FIGURE READINGS

FIG. 1. Overexpression of homologous angiotensin I-converting enzyme (ECA-2) by adenoviral transduction in cultured cardiomyocytes Cultured cardiomyocytes were transducted with an adenovirus overexpressing ACE-2, using different multiplicity of infection (MOD. The MOIs used were, lane 1: MOI=0, lane 2: MOI=1000, lane 3: MOI=2000, lane 4: MOI=3000; lane 5: M01=4000. After 48 h of incubation at 37° C. in an incubator with 5% $CO_2$/95% air, cells were lysated and subjected to polyacrylamide gel electrophoresis in the presence SDS followed by Western blot, using an anti-ACE2 polyclonal antibody.

Figure 2:
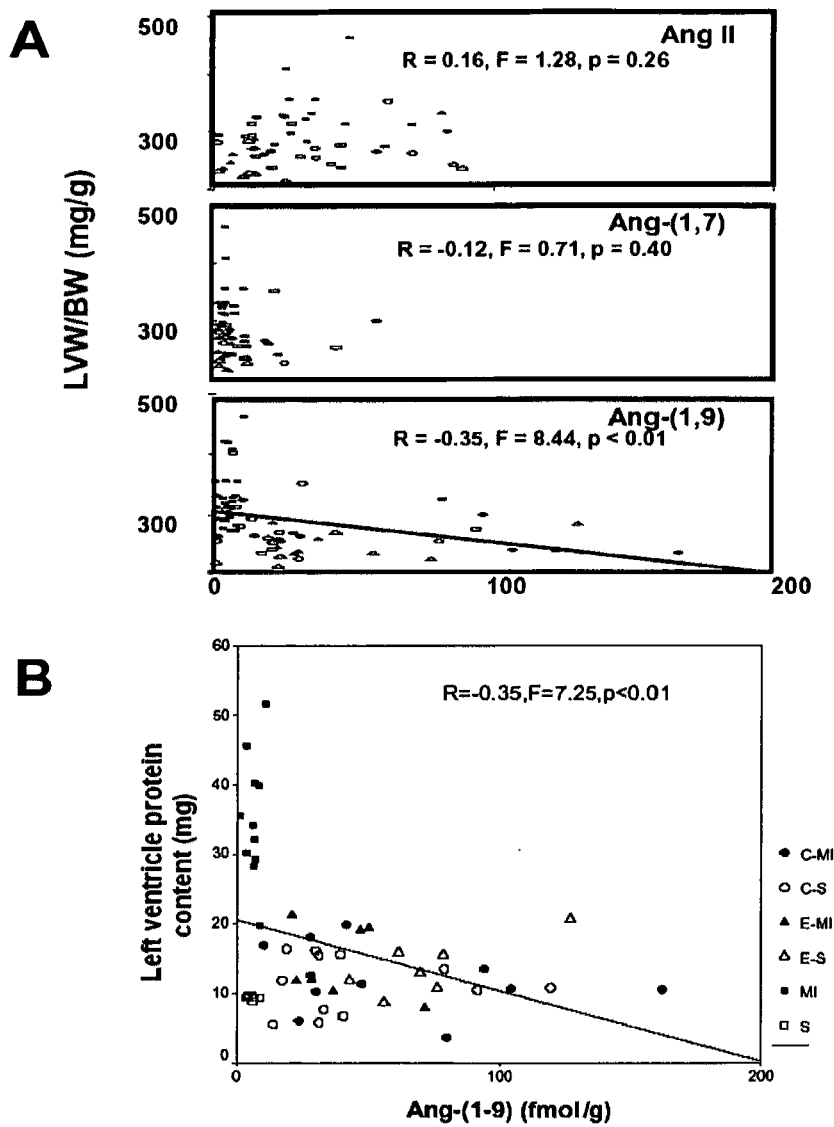

FIG. 2. Correlation of plasma angiotensin-(1-9), angiotensin-II or angiotensin-(1-7) levels with left ventricular hypertrophy (LVH) and protein levels In animal models already described in example 1, plasma angiotensin-(1-9) [Ang-(1-9)], angiotensin-(1-7) [Ang-(1-7)] and angiotensin II [Ang II] levels were described as in example 5. At the same time, left ventricular hypertrophy was determined by left ventricular weight [LVW] and body weight [BW] ratio, or by left ventricle total protein content (see example 3). In panel A) correlations between LVW/BW ratio and plasma Ang II, Ang-(1-7) and Ang-(1-9) levels are shown. In panel B) correlation between left ventricle total protein content and plasma Ang-(1-9) levels are shown. Statistical analysis was performed using the Pearson correlation.

Figure 3:
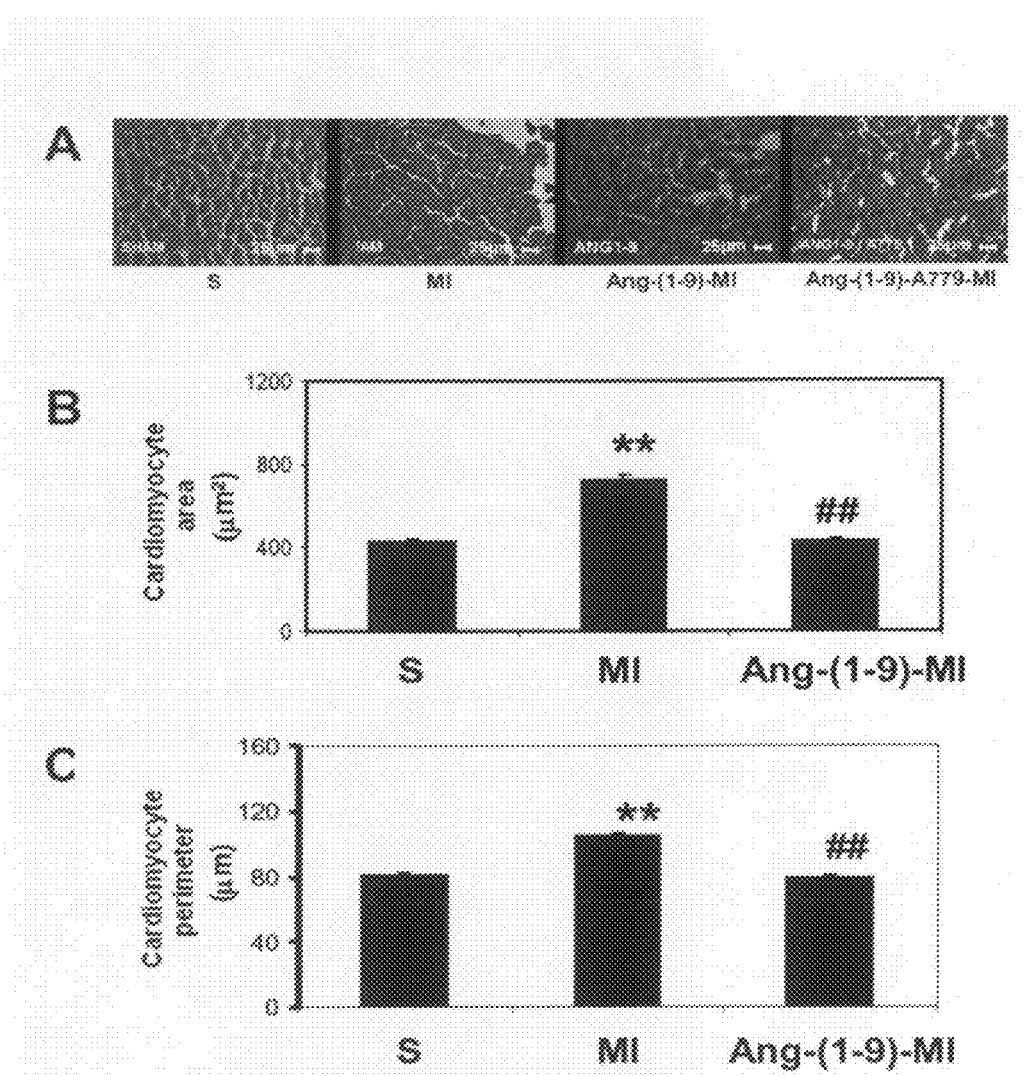

FIG. 3. Angiotensin-(1-9) prevents cardiac hypertrophy development determined by the cardiomyocyte area and perimeter In animal models as described in example 1, heart was removed, histological cuts were made and a morphologic and morphometric analysis was performed on cardiac tissue according to the procedure described in example 3. Panel A) depicts representative figures of histological cuts of sham rats (S), infarcted rats (MI), infarcted rats treated with angiotensin-(1-9) (Ang-(1-9)-MI), and infarcted rats treated with angiotensin-(1-9) and A778 (Ang-(1-9)-A779-MI). In panel B), quantification is illustrated. **p<0.01 vs sham; ##p<0.01 vs MI.

Figure 4:
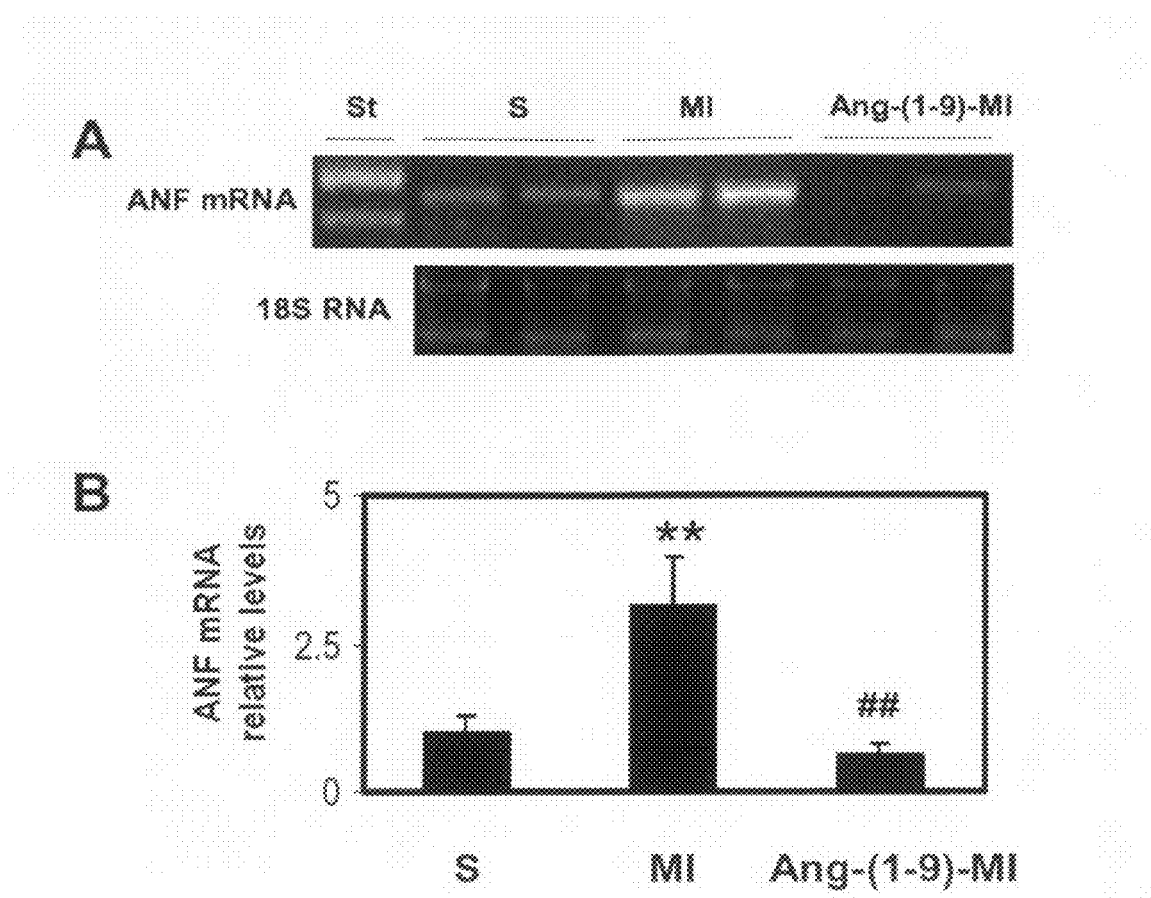

FIG. 4. Angiotensin-(1-9) prevents the development of cardiac hypertrophy determined by auricular natriuretic factor (ANF) mRNA levels In animal models as described in example 1, the heart was removed and RNA was purified according to the procedure described in example 3. Later, the amount of ANF mRNA was determined by reverse transcription followed by polymerization chain reaction (RT-PCR) (see example 3). Panel A) illustrates a representative agarose gel corresponding to amplified RT-PCR for ANF RNA obtained from left ventricle of sham rats (S), infarcted rats (MI), and infarcted rats treated with angiotensin-(1-9) (Ang-(1-9)-MI), and respective loading controls with 18S ribosomal RNA. Panel B) illustrates RT-PCRs quantification. **p<0.01 vs sham; ##p<0.01 vs MI.

Figure 5:
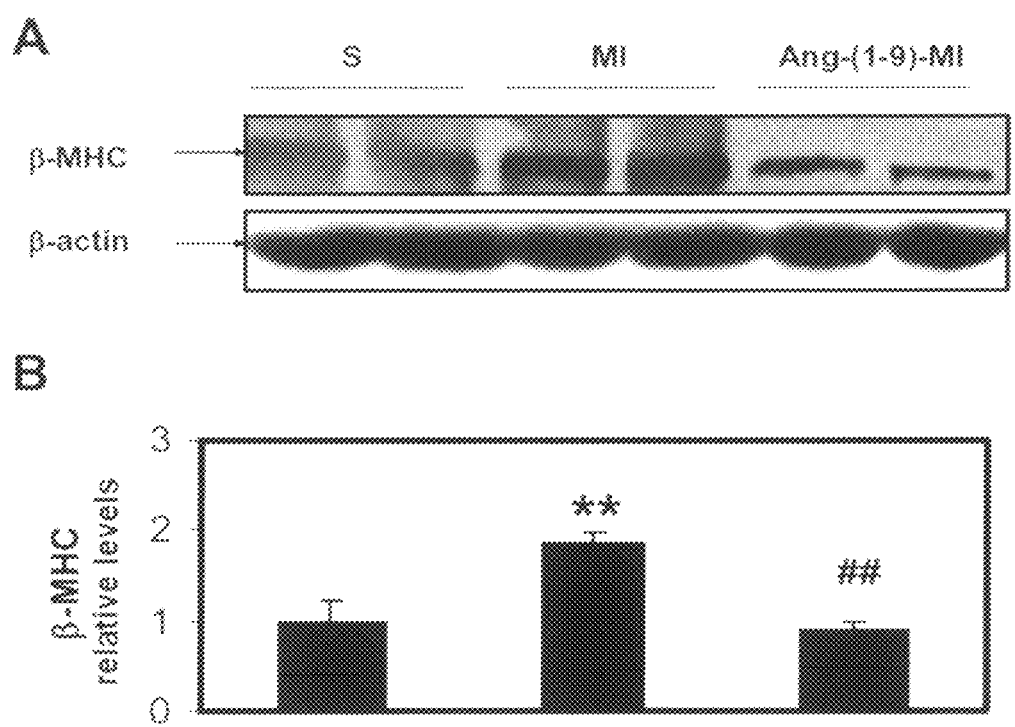

FIG. 5. Angiotensin-(1-9) prevents the development of cardiac hypertrophy determined by β-myosin heavy chain (β-MHC) levels In animal models as described in example 1, heart was removed, and total protein was obtained according to the procedure described in example 3. Then, proteins were resolved by polyacrylamide-SDA electrophoresis, and they were transferred to nitrocellulose membranes. β-MHC was determined by using specific antibodies as described in example 3. Panel A) illustrates a representative Western blot of β-MHC levels in left ventricles of sham rats (S), infarcted rats (MI), and infarcted rats treated with angiotensin-(1-9) (Ang-(1-9)-MI). Additionally, respective loading controls with β-actin are shown. Panel B) illustrates western blots quantification. **p<0.01 vs sham; ##p<0.01 vs MI.

FIG. 6. Angiotensin-(1-9) antagonizes the development of cultured cardiomyocyte hypertrophy induced by IGF-1 and norepinephrine Cultured cardiomyocytes freshly obtained were allowed to adhere to the plate, incubating them for 24 h in culture medium (DME:M199=4:1), supplemented by 5% fetal bovine sereum plus 10% calf serum. Then, medium was replaced by a culture medium without serum and were incubated for further 18 h. Cells were then preincubated with angiotensin-(1-9) (10 and 100 μM) for 1 h, followed by the addition of norpinephrine (NE, 10 μM final) or insulin-like growth factor 1 (IGF-1, 10 nM final) and were incubated for further 48 h. Cells were fixed with 4% formaldehyde, permeabilized with triton X-100 0.2% in PBS for 6 min, and were blocked with 3% BSA in PBS for 1 h. Actin cytoskeleton was revealed by phalloidin-rhodamine (1:400, red color) and nucleus was stained with Hoescht (1:1000, blue color) for 1.5 h. Cells were visualized using an epifluorescence microscope. Figures are representative of 3 separate experiments. Bar corresponds to 50 μM.

What is claimed is:

1. A method of inhibiting, and/or reducing cardiovascular remodeling comprising the steps of:
    providing a pharmaceutical composition comprising an effective amount of angiotensin-(1-9), an angiotensin I-converting enzyme (ACE2) expressing vector and at least one from the group consisting of pharmaceutically acceptable carrier, excipient, stabilizer, diluent, and adjuvant; and
    administering the composition for at least one of inhibiting, and reducing cardiovascular remodeling in any mammal.

2. The method of claim 1 wherein cardiovascular remodeling is selected from the group consisting of cardiac fibrosis, cardiomyocyte hypertrophy, and/or fibroblast proliferation.

3. The method of claim 1 wherein the cardiovascular remodeling is selected from the group consisting of vascular fibrosis, vascular smooth muscle cell proliferation, and/or fibroblast proliferation.

4. The method of claim 1, wherein the at least one from the group consisting of pharmaceutically acceptable carrier, excipient, stabilizer, diluent, and adjuvant is a carrier.

5. The method of claim 4, wherein the carrier is selected from the group consisting of water, saline, dextrose solution, glycol solution, peanut oil, soybean oil, mineral oil, sesame oil, corn oil, and sunflower oil.

6. The method of claim 1, wherein the at least one from the group consisting of pharmaceutically acceptable carrier, excipient, stabilizer, diluent, and adjuvant is a diluent.

7. The method of claim 6, wherein the diluent is selected from the group consisting of water, saline, dextrose solution, glycol solution, peanut oil, soybean oil, mineral oil, sesame oil, corn oil, and sunflower oil.

8. The method of claim 1, wherein the at least one from the group consisting of pharmaceutically acceptable carrier, excipient, stabilizer, diluent, and adjuvant is an excipient.

9. The method of claim 8, wherein the excipient is selected from the group consisting of starch, cellulose, talc, glucose, lactose, sucrose, gelatin, malt, rice, flour, chalk, silica gel, magnesium stearate, glycerol monostearate, sodium chloride, dried skin milk, glycerol, propylene glycol, water, and ethanol.

* * * * *